(12) United States Patent  
Grauhan et al.

(10) Patent No.: US 9,278,197 B2
(45) Date of Patent: Mar. 8, 2016

(54) SLITTER TOOL

(75) Inventors: Ole Grauhan, Berlin (DE); Tassilo Landgraf, Berlin (DE); Ramona Braun, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 1038 days.

(21) Appl. No.: 13/413,036

(22) Filed: Mar. 6, 2012

(65) Prior Publication Data

US 2012/0227561 A1   Sep. 13, 2012

Related U.S. Application Data

(60) Provisional application No. 61/533,800, filed on Sep. 13, 2011.

(30) Foreign Application Priority Data

Mar. 10, 2011  (DE) .......................... 10 2011 001 191

(51) Int. Cl.
*B21F 13/00*  (2006.01)
*A61M 25/06*  (2006.01)
*B26D 3/00*  (2006.01)
*B26D 7/02*  (2006.01)

(52) U.S. Cl.
CPC ........... *A61M 25/0668* (2013.01); *B26D 3/001* (2013.01); *B26D 7/02* (2013.01); *A61M 2025/0675* (2013.01); *Y10T 83/7513* (2015.04)

(58) Field of Classification Search
CPC ..................... A61M 2025/0675; A61M 25/00; A61M 25/0668; B26D 7/02; B26D 3/001

USPC .......................... 606/206, 210; 30/90.4–90.8; 604/161–164.05

See application file for complete search history.

(56) References Cited

U.S. PATENT DOCUMENTS

| 4,687,469 | A | 8/1987 | Osypka |
| 5,330,460 | A | 7/1994 | Moss et al. |
| 6,497,681 | B1 * | 12/2002 | Brenner .................. 604/164.05 |
| 7,338,481 | B2 | 3/2008 | Gardeski et al. |
| 2004/0097888 | A1 * | 5/2004 | Gutierrez ...................... 604/264 |
| 2005/0182435 | A1 | 8/2005 | Andrews et al. |
| 2006/0190013 | A1 * | 8/2006 | Menn ............................ 606/142 |
| 2009/0049698 | A1 | 2/2009 | Drake et al. |
| 2009/0054840 | A1 * | 2/2009 | Drake et al. .................. 604/161 |

OTHER PUBLICATIONS

European Search Report and Notes to the European Search Report on European Patent Application No. EP 12 15 6179, dated May 25, 2012 (8 pages).

* cited by examiner

*Primary Examiner* — Richard Louis
(74) *Attorney, Agent, or Firm* — Buchanan Ingersoll & Rooney PC

(57) ABSTRACT

Slitting tool for slitting open a catheter shaft, including a housing, a blade fastened on the housing, a pushbutton, which is mounted so it is displaceable on the housing, and clamping forceps, which are mounted so they are movable on the housing. The clamping forceps are partially located inside the housing, and include two clamping legs, which are connected to one another at their base located in the housing and have a mutual pre-tension, and which cause the fixation of an electrode line on their periphery located outside the housing, such that the pushbutton, which is mounted so that it is displaceable, and the clamping forceps, which are mounted so that they are movable, act together with one another in such a manner that an actuation of the pushbutton causes an opening of the fixation in the periphery of the clamping forceps.

17 Claims, 3 Drawing Sheets

SLITTER TOOL

CROSS-REFERENCE TO RELATED APPLICATIONS

This patent application claims the benefit of co-pending German Patent Application No. 10 2011 001 191.9, filed on Mar. 10, 2011 in the German Patent Office, and co-pending U.S. Provisional Patent Application No. 61/533,800, filed on Sep. 13, 2011 in the U.S. Patent Office, the disclosures of which are hereby incorporated by reference in their entirety.

TECHNICAL FIELD

The present inventive disclosure relates to a slitter tool for slitting catheters during, for example CRT implantations, also referred to as a slitter tool.

BACKGROUND

During the implantation of electrode lines, insertion catheters are used, in which the electrode line to be implanted is located. The internal diameter of the insertion catheter is adapted to the external diameter of the electrode line. The insertion catheter is first guided into the affected vessel, and the electrode line is subsequently implanted in the vessel through the insertion catheter.

The electrode line has an electrode, or electric, plug on the proximal end thereof, which is used for the electrical connection to an electro-medical implant. This plug typically has an external diameter which is larger than the internal diameter of the insertion catheter. However, since the insertion catheter—as indicated by the name—is only used for inserting the electrode line, it must be removed again. Simple pulling of the insertion catheter in the proximal direction is not possible because of the electrode plug.

Slitter tools are used to open up the insertion catheter, in order to remove it over the electrode plug when it is no longer needed. The insertion catheter is slit along the length with the aid of a blade located on the slitter tool and then removed. It is problematic, in this procedure, that the electrode line which was just implanted can also slip. In order to prevent this, manifold clamping mechanisms are known. An example of this can be inferred from U.S. Pat. No. 4,687,469 or U.S. Pat. No. 7,338,481, in which the electrode line is manually fixed using a finger of the operator on the slitting tool and the insertion catheter is pulled away over it. It is disadvantageous, in this case, that the manual fixation is very unreliable, and slipping of the electrode line which is already implanted can unintentionally occur. Furthermore, in this solution, the electrode line can be damaged by buckling. In addition, the solutions are typically not suitable for different electrode line diameters, because the clamp guide in which the electrode line is fixed by means of the pressure of the thumb, for example, is only dimensioned for specific diameters. This can result in slipping, in particular in the case of excessively small diameters.

The semi-manual fixation mechanism from U.S. Pat. No. 6,497,681, which is based on clamping forceps, by means of which the electrode line is fixed, is also susceptible to interference. For this purpose, the operator must actively press together the clamping forceps, in order to thus fix the electrode line between the clamping forceps legs. Unintentional opening can also occur here; however, the problem of buckling of the electrode line has been minimized.

A further proposed solution is known from U.S. Publication No. 2009/0049698, in which the fixation of the electrode line is performed by means of a fastening arm on the housing of the slitter tool. The fixation is caused by the actuation of a pushbutton, so that the operator must exert a constant finger pressure on this pushbutton during the slitting procedure. This solution is not practical for the operator, since it is very strenuous. This can, in turn, result in incorrect behavior which damages the electrode.

In view of the background of the mentioned disadvantages of the prior art, there is a need for a slitter tool which offers reliable, slip-proof fixation of electrode lines having different diameters with simultaneously simplified handling and avoidance of electrode line damage.

The present inventive disclosure is directed toward overcoming one or more of the above-identified problems.

SUMMARY

The slitter tool according to a first embodiment of an object of the patent application comprises a housing, a blade fastened on the housing, a pushbutton, which is located on the housing and can be externally actuated, and clamping forceps in the housing having two (clamping) legs, which are changeable in their location in relation to the housing. The legs of the clamping forceps are shaped so that they move from a base, on which both legs are fastened to one another, away from one another in the direction of a periphery, in which the electrode line is fixed, so that the distance between both legs is expanded. In the idle state of the clamping forceps, each leg causes a force through a pre-tension, which is oriented toward the respective, other leg and, thus, causes clamping on the periphery. The location change of the clamping forceps is performed by actuating the pushbutton.

An object of the first embodiment is distinguished in that a spreading element is also fixedly mounted in the housing. The pushbutton, the spreading element, and the clamping forceps act together with one another in such a manner that an actuation of the pushbutton cancels the idle state of the clamping forceps and causes opening of the fixation in the periphery of the clamping forceps, in that the two legs are moved away from one another by the spreading element.

According to a second embodiment, the clamping forceps just described are fixedly connected to the housing, and the spreading element is mounted so it is displaceable. The pushbutton, the spreading element, and the clamping forceps also work together with one another here in such a manner that an actuation of the pushbutton cancels the idle state of the clamping forceps and causes opening of the fixation in the periphery of the clamping forceps, in that the two legs are moved away from one another by the spreading element.

In both embodiments, the periphery of the clamping forceps is formed by the open ends of the clamping legs of the clamping forceps. These are shaped so that they allow the fixation of the electrode line, which is located inside the catheter, effectively and securely. These open ends of the clamping legs preferably each consist of a round or prismatic half-shell for accommodating the electrode line, whereby the fixation of the electrode line during the slitting open of the catheter is achieved.

In order that the catheter can be slit open along its longitudinal axis, the catheter must be positioned in relation to the blade so that the blade is located substantially in the radial direction to the catheter cross-section. Therefore, the two above-mentioned half-shells of the clamping forceps form an enclosed cylindrical space in the idle state, which has a longitudinal axis that is arranged so that the electrode line located in this space and, therefore, also the catheter are positioned to the blade so that the blade can slit open the catheter in its longitudinal direction.

In order to make the slitting movement still more reliable, the blade comprises a guide, which extends parallel to the longitudinal axis of the half-shell and which prevents yielding of the catheter away from the blade during the slitting. For this purpose, this guide is located at the open end of the blade, i.e., on the side which protrudes away from the housing. The blade is located between the guide and the housing. The catheter can thus be inserted between the guide and the housing.

A central function of the described slitting tool is assigned to the pushbutton, which has a first position protruding out of the housing in the idle state, and a second position located in the housing after the actuation and, therefore, causes the fixation to be opened. The interaction with the spreading element and the clamping forceps is achieved by the actuation of this pushbutton, which finally results in the movement of the two legs away from one another. Because, in contrast to the solutions in the prior art, the mechanism and, therefore, the force application to the system are first needed to disengage the fixation, the handling is simplified.

In order that the clamping forceps return back into the idle state, while the system made of the pushbutton, spreading element, and clamping forceps still remains able to be actuated, one or more reset elements are provided, which cause a return movement of the pushbutton from the second position into the first position (idle state). The reset elements can be springs, in particular, coiled springs, which act between the housing and the pushbutton. Since the pushbutton is connected to the triggering element—i.e., either to the spreading element or to the clamping forceps—a return of the pushbutton into the first position results in closing of the fixation.

Upon actuation of the pushbutton, a mutual displacement of the clamping forceps and the spreading element is achieved. In particular, the spreading element and the base of the clamping forceps are displaced toward one another. Through the above-described reset elements, this procedure is reversible at any time without force action, whereby simple handling by the operator is made possible.

The spreading element is typically located between the two legs, so that it can act on the two legs upon actuation of the pushbutton and thus press or deflect the legs outward. The spreading element can occupy the cross-section of a triangle, with one of the corners pointing in the direction of the base of the clamping forceps. In this manner, the actuation is thus made easier. A spreading element, which is fixedly connected to the housing, is located between the two legs in the section in which the distance is expanded. Upon actuation of the pushbutton, the two legs also move in relation to the spreading element, which is positioned and dimensioned so that it presses the two legs away from one another. In this manner, the clamping is thus canceled.

As described above, an object of the inventive disclosure generally comprises two embodiments. According to the variant designated above as the first embodiment, the clamping forceps are variable in their location in relation to the housing, while the spreading element is fixedly mounted, i.e., fixedly connected to the housing. The spreading element is preferably fixedly mounted between the two legs of the clamping forceps.

In this embodiment, the pushbutton is thus connected to the clamping forceps, so that the actuation of the pushbutton causes a displacement of the base of the clamping forceps in the direction of the spreading element fixed in the housing, so that the two legs are pressed away from one another. This means that the clamping forceps are displaceable in at least one direction, and preferably in the direction of their longitudinal extension parallel to their clamping legs, and the above-mentioned movement of the clamping legs thus occurs.

Furthermore, the clamping forceps preferably move upon actuation of the pushbutton in the direction of their periphery located outside the housing, so that they move away from the housing. Since the two legs also move away from one another because of the spreading element, this makes it easier for the operator to insert the electrode line into the periphery of the clamping forceps.

In order to make the handling easier still, the periphery moves due to the movement of the pushbutton back into its first position and back toward the housing because of the reset elements, whereby the opening is closed and the fixation is produced.

Further designs of the slitter tool are conceivable. Thus, for example, it is conceivable that the spreading element forms a section of the fixation, i.e., the spreading element is attached to the housing so that the clamping forceps press the catheter against the spreading element during the movement toward the housing, and the fixation is thus reinforced still further and therefore becomes more secure.

In the above-mentioned second embodiment, in which the spreading element is connected to the pushbutton and is therefore displaceable, the actuation of the pushbutton results in a displacement of the spreading element in the direction of the base of the clamping forceps, which is fixedly mounted in the housing, whereby the two legs are caused to be pressed away from one another.

According to a further variant of this embodiment, the spreading element occupies the position between the two legs upon actuation of the pushbutton. For example, the spreading element is then located, in the first position of the pushbutton, laterally to the gap between the two legs of the clamping forceps. By actuating the pushbutton and moving it into the second position, the spreading element moves into the space between the two legs, whereby the legs are moved away from one another and therefore the clamp is opened.

The fixation of the electrode line runs as follows: A clamp (fixation) having a variable diameter is selected. This is only possible through active actuation of the pushbutton, whereby the clamping forceps are opened. An electrode line is inserted. The pushbutton is subsequently released, whereby the clamping forceps return back into the idle state and the electrode line is clamped. It is unimportant, in this case, which diameter the electrode line has.

The design of the clamp on the periphery of the clamping forceps is formed so that the electrode line is clamped well in the direction of the slit. Because of a slight opening of the half-shells in the forward area, the clamping forces are less at a right angle to the slit direction. This allows automatic disengagement of the electrode line from the fixation if the slitting tool tilts. The slitting tool is held in the same plane as the catheter handle (parallel to one another). Furthermore, the holding point, at which the thumb and index finger hold the slitting tool, is at the same height or even in front of the blade. These two points minimize tilting. A pulling movement, and not a thrust movement, is executed using the slitting tool. Therefore, it centers automatically and tilts less.

The fixation is formed in such a manner that reinsertion of the slitting tool into the catheter is possible without problems.

Various other objects, aspects and advantages of the present inventive disclosure can be obtained from a study of the specification, the drawings, and the appended claims.

DESCRIPTION OF THE DRAWINGS

Further possible embodiments are shown in the drawings. The present invention is explained in the following in greater detail as an example, with reference to exemplary embodiments depicted in drawings. In the drawings.

DETAILED DESCRIPTION

Figure 1:
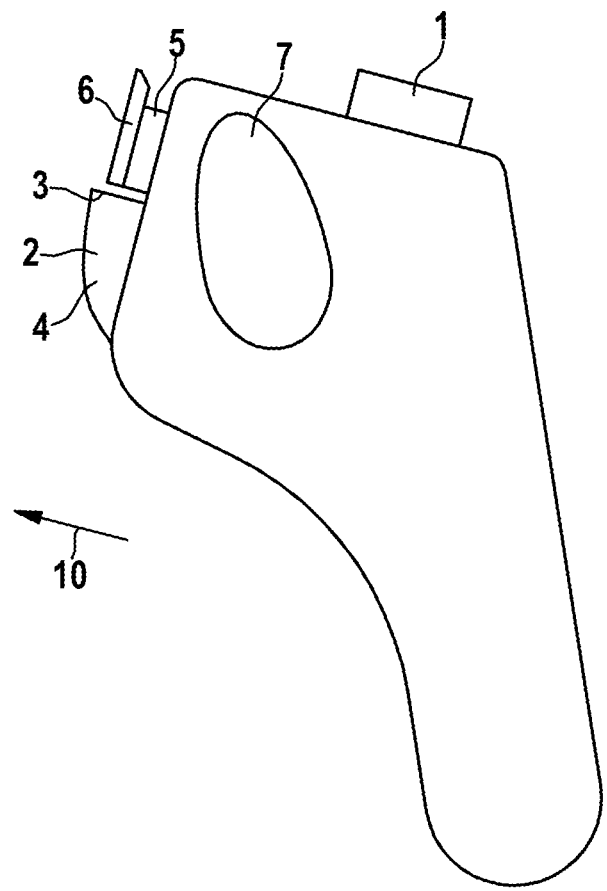
FIG. 1 shows the slitter tool according to a first embodiment in a side view.

FIG. 1 shows the slitter tool of the first embodiment in a side view. A pushbutton 1 is connected to clamping forceps 2. If the pushbutton 1 is pressed, this results in a movement of the clamping forceps 2 out of the housing. In FIG. 1, this movement is executed in the left direction 10. Due to this movement, the clamping forceps 2 open, i.e., the visible periphery having the external and open clamping forceps legs opens, in that they move away from one another. The opening of the clamping legs 2 is caused by a spreading element 8, which is located between the two legs and via which the clamping forceps 2 are displaced. The spreading element 8 can be attached to the housing or to the blade 5.

When the electrode line 11 is inserted (see FIGS. 3A-3B), the pushbutton is released. The clamping forceps 2 return back into the idle state. The return into the idle state is caused by one or more springs, which retract the clamping forceps 2 into the housing.

A blade 5 for slitting open the catheter shaft along its longitudinal axis is located in the direction before the fixation. An electrode guide 6, which can be injection-molded from plastic or metal, is additionally attached to the blade 5. The blade 5 can either be inserted together with the guide 6 or can also be extrusion-coated during the production of the guide 6. The formation made of blade 5 and electrode guide 6 can be inserted into the housing or connected directly thereto.

The holding point 7 (position of thumb and index finger) is located in front of, or at the height of, the blade 5.

The periphery of the clamping legs 2 forms a clamp, which is formed from two round or prismatic half-shells to accommodate the electrode line.

Figure 2:
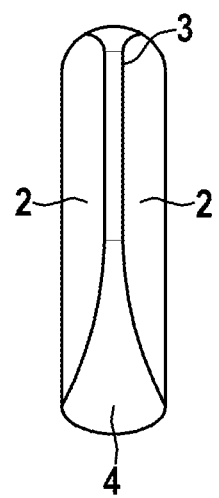
FIG. 2 shows a top view of the periphery of the clamping forceps of the slitter tool.

FIG. 2 shows a top view of the periphery of the clamping forceps 2, in which the electrode line 11 can be inserted and fixed. The two legs 2 of the clamping forceps are recognizable. At the front end 3, pointing in the direction of the blade 5, the legs 2 are shaped so that the clamping gap is reduced. The clamp encloses the electrode line therein. Through this shaping, automatic disengagement of the electrode line 11 is possible upon tilting of the slitting tool, which results in avoidance of electrode damage. In addition, this design has the result that the slitter tool can be inserted back into the catheter without problems. At the rear end 4, pointing away from the blade 5, the legs 2 are shaped so that the clamping gap is enlarged, whereby the insertion of the electrode line is made easier.

Figure 3A:
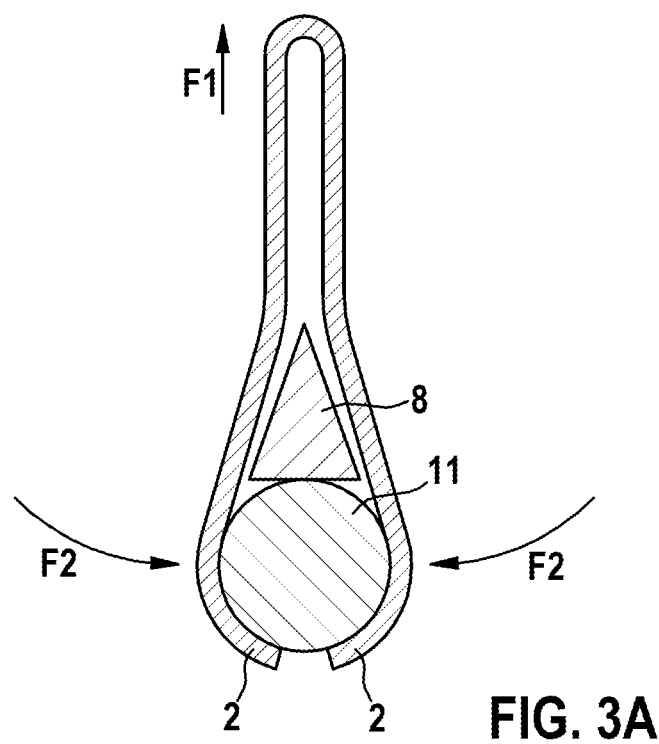
FIGS. 3A and 3B show a schematic view of the clamping mechanism according to the first embodiment of the slitter tool.
Figure 3B:
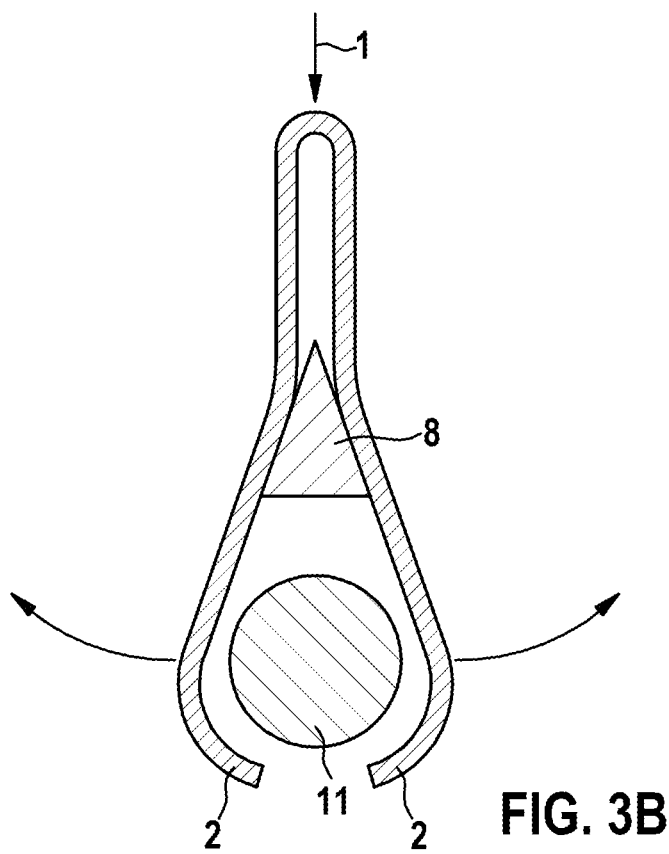
Figure 4:
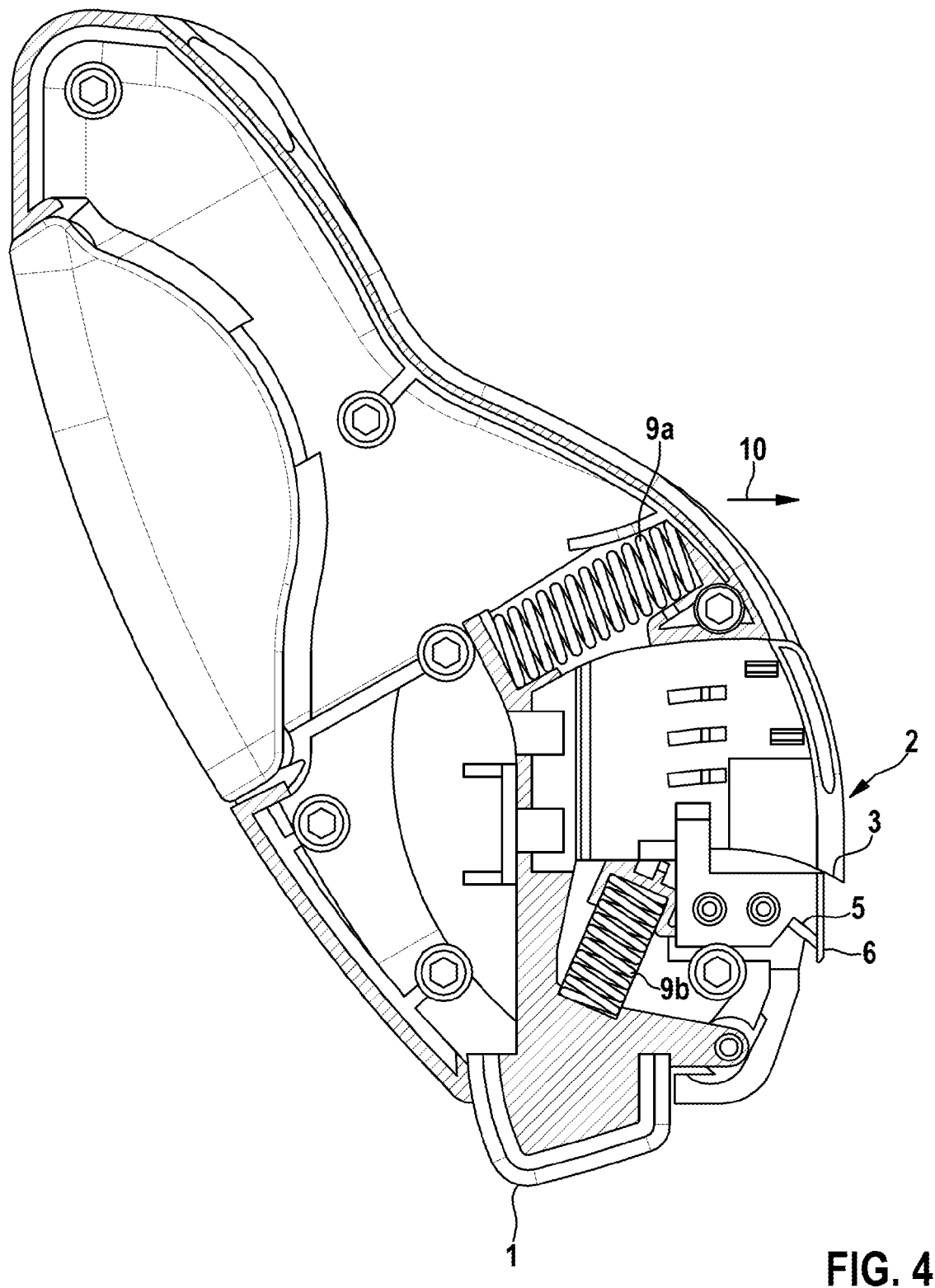
FIG. 4 shows a cross-sectional view according to the first embodiment of the slitter tool.

FIGS. 3A and 3B show a schematic view of the clamping mechanism according to a first embodiment. FIG. 3A shows the clamping forceps 2 in the idle state having applied legs. Forces F1 and F2 act in the directions indicated by the arrows, whereby the electrode line 11, which is shown in section, is pressed either against the housing of the slitting tool or against the stationary spreading element 8. While the forces F2 are caused by the pre-tension of the legs 2, the force F1 is caused by springs, as identified by 9a and 9b in FIG. 4, for example. Both spring actions are canceled by the actuation of the pushbutton 1.

FIG. 3B shows the clamping forceps 2 in the activated state, when the fixation of the electrode line 11 is canceled. The force F1 is canceled and the clamping forceps 2 are moved relative to the housing and to the spreading element 8 by the actuation of the pushbutton 1. The spreading element 8 in turn causes the cancellation of the forces F2, whereby the legs of the clamping forceps 2 move away from one another and cancel the fixation of the electrode line 11.

Exemplary advantages of the subject(s) of the present inventive disclosure are: On the other hand, the electrode line 11 must be able to disengage from the clamp perpendicularly to the slit direction, when the slitting tool slips out of the catheter. Furthermore, the design should be selected so that tilting of the slitting tool is minimized.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A slitting tool for slitting open a catheter shaft, said slitting tool comprising:
   a housing;
   a blade fastened on the housing;
   a pushbutton, which is externally actuated on the housing; and
   clamping forceps, which are mounted so they are movable or fixed in the housing, the clamping forceps being partially located inside the housing and including two clamping legs, which are connected to one another at their base located in the housing, and have a mutual pre-tension, and which cause the fixation of an electrode line in an idle state on their periphery located outside the housing, wherein a spreading element is also mounted so it is displaceable or fixed in the housing, and wherein the pushbutton, the spreading element, and the clamping forceps work together with one another in such a manner that an actuation of the pushbutton cancels the idle state of the clamping forceps and causes opening of the fixation in the periphery of the clamping forceps, in that the two clamping legs are moved away from one another by the spreading element, and
   wherein the pushbutton has a first position protruding out of the housing in the idle state and a second position located in the housing after the actuation.

2. The slitting tool according to claim 1, wherein one or more reset elements cause a return movement of the pushbutton from the second position into the first position.

3. The slitting tool according to claim 2, wherein the one or more reset elements comprise one or more springs which act between housing and pushbutton.

4. The slitting tool according to claim 3, wherein the springs comprise helical springs.

5. The slitting tool according to claim 1, wherein the actuation of the pushbutton causes a mutual displacement of the clamping forceps and the spreading element.

6. The slitting tool according to claim 5, wherein the spreading element and the base of the clamping forceps are displaced toward one another upon actuation of the pushbutton.

7. The slitting tool according to claim 5, wherein the spreading element is positioned between the two legs of the clamping forceps, or occupies the position between the two legs, upon actuation of the pushbutton.

8. The slitting tool according to claim 5, wherein the pushbutton is connected to the spreading element, so that the actuation of the pushbutton causes a displacement of the spreading element in the direction of the base of the clamping forceps, which is fixedly mounted in the housing, so that the two legs are pressed apart from one another.

9. A slitting tool for slitting open a catheter shaft, said slitting tool comprising:
    a housing;
    a blade fastened on the housing;
    a pushbutton, which is externally actuated on the housing; and
    clamping forceps, which are mounted so they are movable or fixed in the housing, the clamping forceps being partially located inside the housing and including two clamping legs, which are connected to one another at their base located in the housing, and have a mutual pre-tension, and which cause the fixation of an electrode line in an idle state on their periphery located outside the housing, wherein a spreading element is also mounted so it is displaceable or fixed in the housing, and wherein the pushbutton, the spreading element, and the clamping forceps work together with one another in such a manner that an actuation of the pushbutton cancels the idle state of the clamping forceps and causes opening of the fixation in the periphery of the clamping forceps, in that the two clamping legs are moved away from one another by the spreading element,
    wherein the actuation of the pushbutton causes a mutual displacement of the clamping forceps and the spreading element, and
    wherein the pushbutton is connected to the clamping forceps, so that the actuation of the pushbutton causes a displacement of the base of the clamping forceps in the direction of the spreading element, which is fixed in the housing, so that the two legs are pressed apart from one another.

10. The slitting tool according to claim 9, wherein the periphery of the clamping forceps located outside the housing moves away from the housing upon actuation of the pushbutton.

11. The slitting tool according to claim 2, wherein the periphery is moved back toward the housing by the pushbutton and because of the one or more reset elements.

12. The slitting tool according to claim 10, wherein the periphery is moved back toward the housing by the pushbutton and because of the one or more reset elements.

13. The slitting tool according to claim 1, wherein the periphery of the clamping forceps is formed by the open ends of the clamping forceps, which each comprise a round or prismatic half-shell to accommodate the electrode line, whereby the fixation of the electrode line during slitting open the catheter is achieved.

14. The slitting tool according to claim 12, wherein the half-shells of the clamping forceps form an enclosed cylindrical space in the idle state, which has a longitudinal axis that is arranged so that the electrode line located in this space and, therefore, the catheter are positioned to the blade so that the blade can slit open the catheter in its longitudinal direction.

15. The slitting tool according to claim 14, wherein the blade has a guide which extends parallel to the longitudinal axis.

16. The slitting tool according to claim 1, wherein the spreading element has a triangular cross-section shape with one corner pointing in a direction of the base of the clamping forceps.

17. The slitting tool according to claim 13, wherein the open ends of the clamping forceps are configured such that clamping forces are less at right angles to the slit opening of the catheter shaft.

* * * * *